(12) United States Patent
Seetharaman et al.

(10) Patent No.: US 10,190,222 B2
(45) Date of Patent: Jan. 29, 2019

(54) CORROSION INHIBITORS

(71) Applicant: Ecolab USA Inc., St. Paul, MN (US)

(72) Inventors: Jothibasu Seetharaman, Cuddalore (IN); Donald A. Johnson, Batavia, IL (US); Anand Harbindu, Shahjahanpur (IN); Deepak Rane, Mumbai (IN); Jeffery M. Atkins, Aurora, IL (US); Hemant Mondkar, Pune (IN); Vaideeswaran Sivaswamy, Pune (IN)

(73) Assignee: Ecolab USA Inc., St. Paul, MN (US)

( * ) Notice: Subject to any disclaimer, the term of this patent is extended or adjusted under 35 U.S.C. 154(b) by 137 days.

(21) Appl. No.: 15/166,511

(22) Filed: May 27, 2016

(65) Prior Publication Data

US 2016/0348251 A1 Dec. 1, 2016

Related U.S. Application Data

(60) Provisional application No. 62/167,658, filed on May 28, 2015.

(51) Int. Cl.
| | |
|---|---|
| *C23F 11/00* | (2006.01) |
| *C23F 11/04* | (2006.01) |
| *C23F 11/16* | (2006.01) |
| *B05D 1/30* | (2006.01) |
| *C23F 11/14* | (2006.01) |
| *C07D 403/04* | (2006.01) |

(52) U.S. Cl.
CPC .......... *C23F 11/149* (2013.01); *C07D 403/04* (2013.01)

(58) Field of Classification Search
CPC ....... C23F 11/182; C23F 11/00; C23F 11/149; C02F 1/00

USPC .............. 422/7, 12–14, 16; 427/420, 427
See application file for complete search history.

(56) References Cited

U.S. PATENT DOCUMENTS

| | | |
|---|---|---|
| 3,408,307 A | 10/1968 | Troscinski et al. |
| 3,615,616 A | 10/1971 | Wilrijk et al. |
| 4,142,029 A | 2/1979 | Illy |

(Continued)

FOREIGN PATENT DOCUMENTS

| | | |
|---|---|---|
| CN | 103436888 A | 12/2013 |
| EP | 0634460 A2 | 1/1995 |

(Continued)

OTHER PUBLICATIONS

F. Zhang et al., Performance and Theoretical Study on Corrosion Inhibition of 2-(4-pyridyl)-benzimidazole for Mild Steel in Hydrochloric Acid, Corrosion Science, Apr. 3, 2012, vol. 61, pp. 1-9.*

(Continued)

*Primary Examiner* — Monzer R Chorbaji
(74) *Attorney, Agent, or Firm* — Leydig, Voit & Mayer, Ltd.

(57) ABSTRACT

Disclosed are novel compounds and methods useful in applications relating to industrial water systems. The compounds of the present invention are nitrogen-containing heterocyclic compounds comprising a benzotriazole covalently bonded to a benzimidazole moiety, and provide enhanced protection against corrosion of metals in aqueous systems. The compounds of the present invention are generally resistant to halogen attack and provide good corrosion resistance in the presence of oxidizing halogen-based biocides.

20 Claims, 4 Drawing Sheets

(56) References Cited

U.S. PATENT DOCUMENTS

| | | | |
|---|---|---|---|
| 4,306,986 | A | 12/1981 | Schiessl |
| 4,395,294 | A | 7/1983 | Hobbins et al. |
| 4,758,312 | A | 7/1988 | Hunt et al. |
| 5,082,611 | A | 1/1992 | Adams et al. |
| 5,128,065 | A | 7/1992 | Hollander |
| 5,156,769 | A | 10/1992 | Cha et al. |
| 5,455,220 | A | 10/1995 | Dedolph |
| 5,744,424 | A | 4/1998 | Dedolph |
| 5,746,947 | A | 5/1998 | Vanderpool et al. |
| 5,874,026 | A | 2/1999 | Pilsits, Jr. et al. |
| 6,103,144 | A | 8/2000 | Cheng |
| 6,203,719 | B1 | 3/2001 | Turcotte et al. |
| 6,379,587 | B1 | 4/2002 | Chen |
| 6,585,933 | B1 | 7/2003 | Ehrhardt et al. |
| 6,646,082 | B2 | 11/2003 | Ghosh et al. |
| 7,393,395 | B2 | 7/2008 | Aiba et al. |
| 7,968,507 | B2 | 6/2011 | Lee et al. |
| 7,972,655 | B2 | 7/2011 | Abys et al. |
| 8,361,237 | B2 | 1/2013 | Wu et al. |
| 9,074,170 | B2 | 7/2015 | Barnes et al. |
| 2003/0063998 | A1 | 4/2003 | Ghosh et al. |
| 2003/0065116 | A1 | 4/2003 | Ghosh et al. |
| 2010/0123100 | A1 | 5/2010 | Gill et al. |
| 2010/0152086 | A1 | 6/2010 | Wu et al. |
| 2010/0163469 | A1 | 7/2010 | Wan et al. |
| 2010/0197136 | A1 | 8/2010 | Shimada et al. |
| 2011/0318929 | A1 | 12/2011 | Mishima et al. |
| 2012/0108489 | A1 | 5/2012 | Miralles |
| 2012/0283163 | A1 | 11/2012 | Barnes et al. |
| 2013/0295292 | A1 | 11/2013 | Bukeikhanova et al. |
| 2014/0044593 | A1 | 2/2014 | Garner |
| 2015/0152329 | A1 | 6/2015 | Seetharaman et al. |
| 2016/0032221 | A1 | 2/2016 | Barnes et al. |

FOREIGN PATENT DOCUMENTS

| | | |
|---|---|---|
| EP | 1288232 A2 | 3/2003 |
| EP | 2199379 A1 | 6/2010 |
| JP | 2002323741 A | 11/2002 |
| JP | 2006-079093 A | 3/2006 |
| KR | 10-2013-0011943 A | 1/2013 |
| KR | 20140020432 A | 2/2014 |
| WO | WO 90/10732 A1 | 9/1990 |
| WO | WO 96/20295 A1 | 7/1996 |
| WO | WO 96/29449 A1 | 9/1996 |
| WO | WO 97/39610 A1 | 10/1997 |
| WO | WO 99/33824 A1 | 7/1999 |
| WO | WO 02/00965 A1 | 1/2002 |
| WO | WO 02/10326 A1 | 2/2002 |
| WO | WO 2010/048139 A2 | 4/2010 |
| WO | WO 2010/048139 A3 | 4/2010 |
| WO | WO 2013/076509 A1 | 5/2013 |
| WO | WO 2013/138278 A1 | 9/2013 |

OTHER PUBLICATIONS

Antonijevic et al., "Copper Corrosion Inhibitors. A review," *Int. J. Electrochem. Sci.*, 3, 2008, pp. 1-28.

Brubaker, Jr., "Metal Tetrazole Complexes: Bis-(5-aminotetrazolato)-copper(II)," Kedzie Chemical Laboratory, Michigan State University and Laboratorio De Fisica Nuclear Universidad De Chile, 82, Jun. 5, 1959, pp. 82-85.

Finšgar et al., "Inhibition of copper corrosion by 1,2,3-benzotriazole: A review," *Corrosion Science*, 52, 2010, pp. 2737-2749.

Khaled et al., "Piperidines as corrosion inhibitors for iron in hydrochloric acid," *Journal of Applied Electrochemistry*, 34, 2004, pp. 697-704.

Khaled, "Studies of iron corrosion inhibition using chemical, electrochemical and computer simulation techniques," *Electrochimica Acta*, 55(22), Jun. 17, 2010, pp. 6523-6532.

Korean Intellectual Property Office, International Search Report in International Patent Application No. PCT/US2016/034629, dated Aug. 18, 2016, 4 pp.

Korean Intellectual Property Office, Written Opinion in International Patent Application No. PCT/US2016/034629, dated Aug. 18, 2016, 8 pp.

Liu et al., "Electromechanical and Quantum Chemical Studies of 5-Substituted Tetrazoles as Corrosion Inhibitors for Copper in Aerated 0.5 M $H_2SO_4$ Solution," *Materials Sciences and Applications*, 2, 2011, pp. 1268-1278.

NALCO Chemical Company, Analytical Report, "Inhibitor AZ8104," Oct. 19, 1999, 6 pp.

NALCO Chemical Company, Analytical Report, "Inhibitor AZ8104," Oct. 5, 1999, 2 pp.

NALCO Chemical Company, Analytical Report, "10% As NaCITT—Research," Oct. 19, 1999, 6 pp.

Oliphant, "Causes of Copper Corrosion in Plumbing Systems," A Review of Current Knowledge, FR/R0007, Sep. 2010, Foundation for Water Research, Bucks, U.K., 35 pp.

Pillard et al., "Toxicity of Benzotriazole and Benzotriazole Derivatives to Three Aquatic Species," *Wat. Res.* 35(2), 2001, pp. 557-560.

Scendo et al., "Adenine as an Effective Corrosion Inhibitor for Stainless Steel in Chloride Solution" *Int. J. Electrochem. Sci.*, 8, 2013, pp. 9201-9221.

Sherif, "Electrochemical and Gravimetric Study on the Corrosion and Corrosion Inhibition of Pure Copper in Sodium Chloride Solutions by Two Azole Derivatives," *Int. J. Electrochem. Sci.*, 7, 2012, pp. 1482-1495.

Solehudin, "Performance of Benzotriazole As Corrosion Inhibitors of Carbon Steel in Chloride Solution Containing Hydrogen Sulfide," *International Refereed Journal of Engineering and Science*, 1(4), Dec. 2012, pp. 21-26.

Téllez et al., "Coordination behavior of benzimidazole, 2-substituted benzimidazoles and benzothiazoles, towards transition metal ions," *ARKIVOC*, Issue in Honor of Prof. Rosalinda Contreras Theurel, ISSN 1551-7012, 2008, pp. 245-275.

Zhang et al., "Performance and theoretical study on corrosion inhibition of 2-(4-pyridyl)-benzimidazole for mild steel in hydrochloric acid," *Corrosion Science*, 61, Apr. 3, 2012, pp. 1-9.

Korean Intellectual Property Office, International Search Report in International Patent Application No. PCT/US2016/034619, dated Apr. 11, 2017, 4 pp.

Korean Intellectual Property Office, Written Opinion in International Patent Application No. PCT/US2016/034619, dated Apr. 11, 2017, 6 pp.

Attayibat, et al., "Quantum chemical studies on N-donors based-pyrazole compounds as corrosion inhibitors for steel in acidic media," *Asian J. Chem* , 21(1), 2009, pp. 105-112.

Bouklah et al., "Pyridine-pyrazole compound as inhibitor for steel in 1 M HCl," *Applied Surface Science*, 240(1-4), Feb. 15, 2015, pp. 341-348.

Eddy et al., "Theoretical and experimental studies on the corrosion inhibition potentials of some purines for aluminum in 0.1 M HCl," *J. of Adv. Research*, 6(2), Jan. 20, 2014, pp. 203-217.

Li et al, "Synergistic inhibition effect of 6-benzylaminopurine and iodide ion on the corrosion of cold rolled steel in $H_3PO_4$ solution," *Corrosion Science*, 53(11), Nov. 2011, pp. 3704-3711.

Ravichandran et al., "Corrosion inhibition of brass by benzotriazole derivatives in NaCl solution," *Anti-Corrosion Methods and Materials*, 52(4), 2005, pp. 226-232.

Scendo, "Corrosion inhibition of copper by purine or adenine in sulphate solutions," *Corrosion Science*, 49(10), Oct. 2007, pp. 3953-3968.

\* cited by examiner

CORROSION INHIBITORS

CROSS-REFERENCE TO RELATED APPLICATION

This patent application claims the benefit of U.S. Provisional Patent Application No. 62/167,658, filed May 28, 2015, which is incorporated by reference in its entirety.

FIELD OF INVENTION

The invention relates to heterocyclic compounds and their use as corrosion inhibitors for metal surfaces in aqueous environments.

BACKGROUND OF THE INVENTION

Copper and copper alloy components are commonly used in industrial systems due to copper's high thermal conductivity and anti-microbial properties. Copper and copper alloys (e.g., bronze and brass) are relatively resistant to corrosion as a result of protective film layers that naturally coat the surface of copper, which include an inner cuprous oxide film layer and an outer cupric oxide film layer. Under anaerobic conditions, these protective layers generally reduce the rate of further corrosion of the metal surface. However, under certain conditions, copper and copper alloys are susceptible to corrosion. In the presence of oxygen and under acidic conditions, oxidation of copper and dissolution of the copper (II) ion into water can occur.

Copper corrosion inhibitors are commonly added to industrial water systems to prevent and reduce dissolution of copper from system surfaces. In particular, the use of nitrogen-containing compounds such as azoles is well known for inhibiting the corrosion of copper and copper alloys. It is generally believed that the nitrogen lone pair electrons coordinate to the metal, resulting in the formation of a thin organic film layer that protects the copper surface from elements present in the aqueous system. Nitrogen-containing compounds such as azoles are also known to precipitate copper (II) from the aqueous solution, hindering corrosion that can occur due to galvanic reactions between copper and other metals.

Oxidizing halogens are commonly used as biocides in industrial systems to control slime and microbiological growth in water. The protective film provided by many azoles erodes in the presence of oxidizing halogens such as chlorine, hypochlorite, and hypobromite, reducing the effectiveness of the corrosion inhibitor. Moreover, a decrease in copper (II) precipitation often occurs in the presence of oxidizing halogens due to halogen attack of the corrosion inhibitor in solution. Thus, in the presence of oxidizing halogens, an excess or continuous injection of corrosion inhibitor is often required to maintain the organic protective film.

It would be desirable to provide a method of using a corrosion inhibitor that provides protection of copper in the absence and presence of oxidizing halogen agents.

BRIEF SUMMARY OF THE INVENTION

In an embodiment, the invention provides a compound of formula (I):

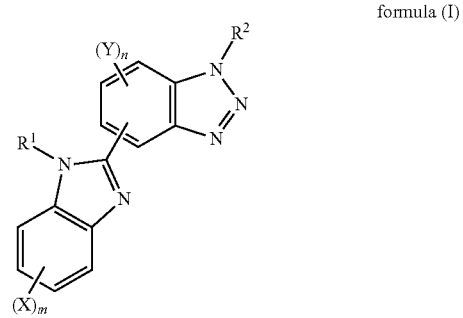

formula (I)

wherein each of X and Y is the same or different, and is selected from the group consisting of hydrogen, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, halosubstituted alkyl, amino, aminoalkyl, cyano, alkoxy, hydroxyl, thiol, alkylthio, carbonyl, nitro, phosphoryl, phosphonyl, and sulfonyl;

each of $R^1$ and $R^2$ is the same or different, and is selected from the group consisting of hydrogen, deuterium, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, hydroxyl, and carbonyl;

m is 1, 2, 3, or 4; and n is 1, 2, or 3;

or a salt thereof.

In another embodiment, the invention provides a method for inhibiting corrosion of a metal surface in contact with an aqueous system, the method comprising adding to the aqueous system a compound of formula (I), wherein each of X and Y is the same or different, and is selected from the group consisting of hydrogen, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, halosubstituted alkyl, amino, aminoalkyl, cyano, alkoxy, hydroxyl, thiol, alkylthio, carbonyl, nitro, phosphoryl, phosphonyl, and sulfonyl; each of $R^1$ and $R^2$ is the same or different, and is selected from the group consisting of hydrogen, deuterium, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, hydroxyl, and carbonyl; m is 1, 2, 3, or 4; and n is 1, 2, or 3; or a salt thereof.

DETAILED DESCRIPTION OF THE INVENTION

Figure 1:
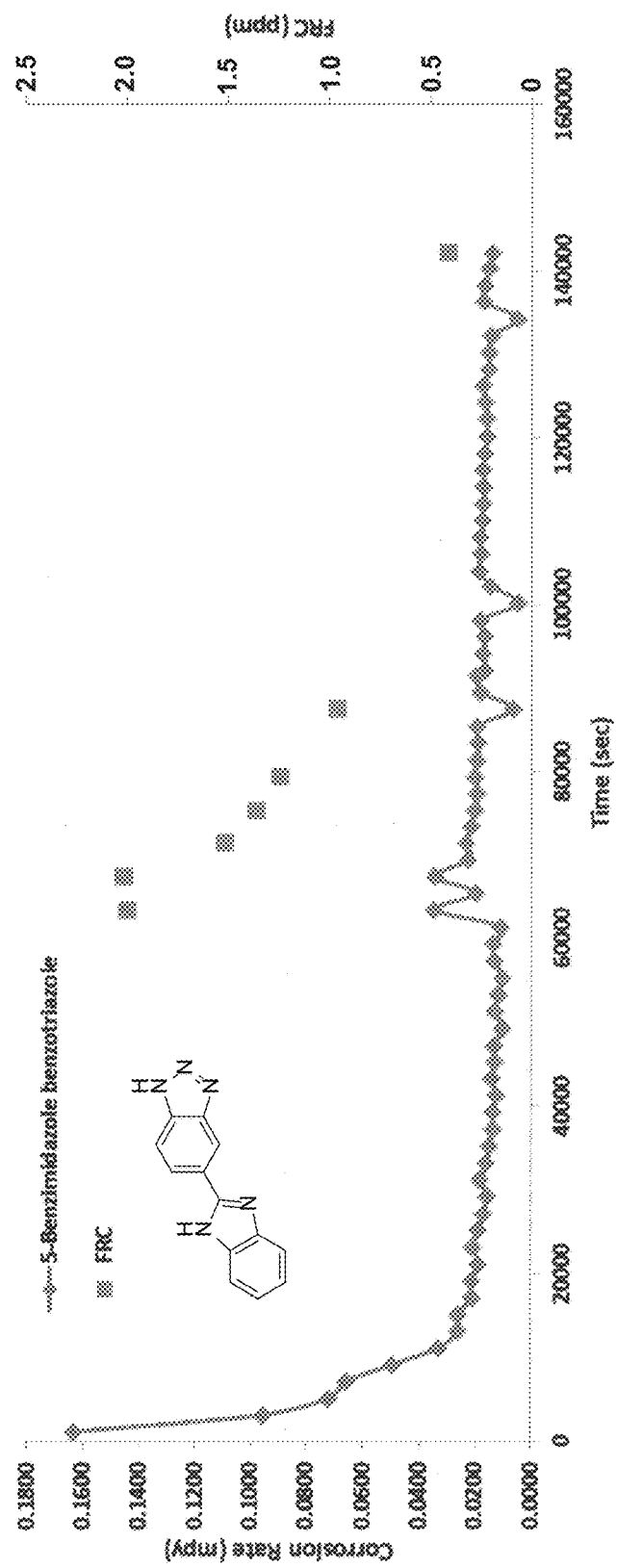
FIG. 1 is a line graph that illustrates the corrosion rate of copper using 5-(1H-benzo[d]imidazol-2-yl)-1H-benzo[d][1,2,3]triazole (5-benzimidazole benzotriazole) as a corrosion inhibitor in the absence and presence of bleach.

The following definitions are provided to determine how terms used in this application, and in particular, how the claims are to be construed. The organization of the definitions is for convenience only and is not intended to limit any of the definitions to any particular category.

"Alkoxy" refers to a moiety of the formula RO—, where R is alkyl, alkenyl, or alkynyl;

"Alkyl" refers to a straight-chain or branched alkyl substituent. Examples of such substituents include methyl, ethyl, propyl, isopropyl, n-butyl, sec-butyl, isobutyl, tert-butyl, pentyl, isoamyl, hexyl, and the like;

"Alkylheteroaryl" refers to an alkyl group linked to a heteroaryl group;

"Alkenyl" refers to a straight or branched hydrocarbon, preferably having 2, 3, 4, 5, 6, 7, 8, 9, 10, 11, 12, 13, 14, 15, or 16 carbons, and having one or more carbon-carbon double bonds. Alkenyl groups include, but are not limited to, ethenyl, 1-propenyl, 2-propenyl (allyl), iso-propenyl, 2-methyl-1-propenyl, 1-butenyl, and 2-butenyl. Alkenyl groups may be unsubstituted or substituted by one or more suitable substituents;

"Alkylthio" refers to a moiety of the formula RS—, where R is alkyl, aryl, alkenyl, or alkynyl;

"Alkynyl" refers to a straight or branched hydrocarbon, preferably having 2, 3, 4, 5, 6, 7, 8, 9, 10, 11, 12, 13, 14, 15, or 16 carbons, and having one or more carbon-carbon triple bonds. Alkynyl groups include, but are not limited to, ethynyl, propynyl, and butynyl. Alkynyl groups may be unsubstituted or substituted by one or more suitable substituents;

"Aminoalkyl" refers to a nitrogen substituent attached to one or more carbon groups, such as alkyl or aryl. For example, the aminoalkyl group can be REIN- (secondary) or $R_2N$- (tertiary) where R is alkyl or aryl;

"Aqueous system" refers to any system containing metal components which are in contact with water on a periodic or continuous basis;

"Aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise 4n+2n electrons, according to Hückel's Rule;

"Carbonyl" refers to a substituent comprising a carbon double bonded to an oxygen. Nonlimiting examples of such substituents include aldehydes, ketones, carboxylic acids, esters, amides, and carbamates;

"Cycloalkyl" refers to a cyclic alkyl substituent containing from, for example, about 3 to about 8 carbon atoms, preferably from about 4 to about 7 carbon atoms, and more preferably from about 4 to about 6 carbon atoms. Examples of such substituents include cyclopropyl, cyclobutyl, cyclopentyl, cyclohexyl, cycloheptyl, cyclooctyl, and the like. The cyclic alkyl groups may be unsubstituted or further substituted with alkyl groups such as methyl groups, ethyl groups, and the like;

"Halogen" or "halo" refers to F, Cl, Br, and I;

"Halosubstituted alkyl" refers to an alkyl group as described above substituted with one or more halogens, for example, chloromethyl, trifluoromethyl, 2,2,2-trichloroethyl, and the like;

"Heteroaryl" refers to a monocyclic or bicyclic 5- or 6-membered ring system, wherein the heteroaryl group is unsaturated and satisfies Hückel's rule. Non-limiting examples of heteroaryl groups include furanyl, thiophenyl, pyrrolyl, pyrazolyl, imidazolyl, 1,2,3-triazolyl, 1,2,4-triazolyl, isoxazolyl, oxazolyl, isothiazolyl, thiazolyl, 1,3,4-oxadiazol-2-yl, 1,2,4-oxadiazol-2-yl, 5-methyl-1,3,4-oxadiazole, 3-methyl-1,2,4-oxadiazole, pyridinyl, pyrimidinyl, pyrazinyl, triazinyl, benzofuranyl, benzothiophenyl, indolyl, quinolinyl, isoquinolinyl, benzimidazolyl, benzoxazolinyl, benzothiazolinyl, quinazolinyl, and the like;

"Industrial water system" means any system that circulates water as its primary ingredient. Nonlimiting examples of "industrial water systems" include cooling systems, boiler systems, heating systems, membrane systems, paper making process or any other system that circulates water as defined below;

"Mild steel" refers to carbon and low alloy steels;

"Oxidizing halogen" refers to an oxidizing agent comprising at least one halogen. Examples of oxidizing halogens include, but are not limited to, chlorine bleach, chlorine, bromine, iodine, hypochlorite, hypobromite, iodine/hypoiodous acid, hypobromous acid, halogenated hydantoins, chlorine dioxide, stabilized versions of hypochlorous or hypobromous acids, and compounds or chemical groups capable of releasing chlorine, bromine, or iodine;

"Water" means any substance that has water as a primary ingredient. Water may include pure water, tap water, fresh water, recycled water, brine, steam, and/or any aqueous solution, or aqueous blend.

For convenience of reference herein, the structure of the compounds of formula (I) is numbered as follows:

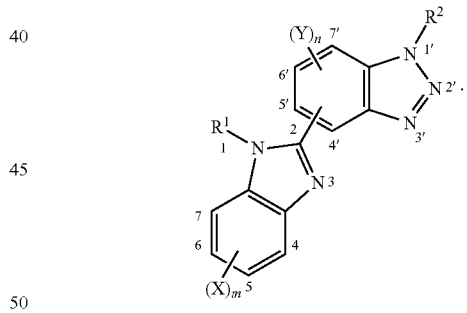

Whenever a range of the number of atoms in a structure is indicated (e.g., a $C_1$-$C_{16}$ alkyl, $C_2$-$C_{16}$ alkenyl, $C_2$-$C_{16}$ alkynyl, etc.), it is specifically contemplated that any sub-range or individual number of carbon atoms falling within the indicated range also can be used. Thus, for instance, the recitation of a range of 1-16 carbon atoms (e.g., $C_1$-$C_{16}$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-16 carbon atoms (e.g., $C_2$-$C_{16}$) as used with respect to any chemical group (e.g., alkyl) referenced herein encompasses and specifically describes 1, 2, 3, 4, 5, 6, 7, 8, 9, 10, 11, 12, 13, 14, 15, and/or 16 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 1-13 carbon atoms, 1-14 carbon atoms, 1-15 carbon atoms, 1-16 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 2-13 carbon atoms, 2-14 carbon atoms, 2-15 carbon atoms, 2-16 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 3-13 carbon atoms, 3-14 carbon atoms, 3-15 carbon atoms, 3-16 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, 4-12 carbon atoms, 4-13 carbon atoms, 4-14 carbon atoms, 4-15 carbon atoms, and/or 4-16 carbon atoms, etc., as appropriate).

The invention provides novel compounds, processes for their preparation, and methods for using the compounds as corrosion inhibitors. The compounds and methods of the present invention are particularly useful for inhibiting corrosion of metallic components in industrial water systems. The compounds of the present invention are nitrogen-containing heterocyclic compounds comprising a benzotriazole covalently bonded to a benzimidazole moiety. While benzotriazoles and benzimidazoles are generally unstable in the presence of oxidizing halogen compounds, Applicants have discovered that a benzotriazoles substituted with benzimidazoles have exemplary stability in the presence of oxidizing halogen compounds. It was surprisingly and unexpectedly discovered that corrosion inhibitors of the present invention can provide greater protection against corrosion than benzimidazole, benzotriazole, and tolyltriazole in the presence of oxidizing halogen compounds. While not wishing to be bound by any particular theory, it is believed that the compounds of the present invention provide a protective film that is essentially impenetrable by common oxidizing halogen compounds. Thus, in certain embodiments, the compounds of the present invention provide protection against metal corrosion in aqueous systems which employ oxidizing halogen compounds as biocides.

In an embodiment, the invention provides a compound of formula (I):

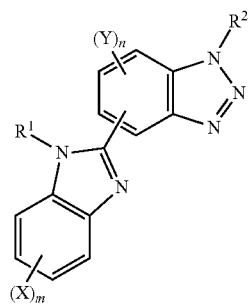

formula (I)

wherein each of X and Y is the same or different, and is selected from the group consisting of hydrogen, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, halosubstituted alkyl, amino, aminoalkyl, cyano, alkoxy, hydroxyl, thiol, alkylthio, carbonyl, nitro, phosphoryl, phosphonyl, and sulfonyl;

each of $R^1$ and $R^2$ is the same or different, and is selected from the group consisting of hydrogen, deuterium, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, hydroxyl, and carbonyl;

m is 1, 2, 3, or 4; and n is 1, 2, or 3;

or a salt thereof.

The X substituent or substituents as shown can occupy any available position on the benzimidazole ring. Thus, in certain embodiments, the X substituent or substituents can be located at the 4-position, 5-position, 6-position, and/or 7-position of the benzimidazole. In certain preferred embodiments, the X substituent is at the 5-position.

The Y substituent or substituents as shown can occupy any available position on the benzotriazole ring. Thus, in certain embodiments, the Y substituent or substituents can be located at the 4'-position, 5'-position, 6'-position, and/or 7'-position of the benzotriazole.

As disclosed above, m can be 1, 2, 3, or 4. If m is 2, 3, or 4, the X substituents can occupy any open position and can be positioned ortho-, meta-, or para- to each other.

As disclosed above, n can be 1, 2, or 3. If n is 2 or 3, the Y substituents can occupy any open position and can be positioned ortho-, meta-, or para- to each other.

In certain preferred embodiments, X and Y are individually chosen electron-rich or a $C_1$-$C_{16}$ alkyl group.

In certain preferred embodiments, $R^1$ and $R^2$ are hydrogen.

In certain preferred embodiments, X is $C_1$-$C_{16}$ alkyl and Y is hydrogen.

In certain preferred embodiments, X and Y are hydrogen.

In certain preferred embodiments, X is methyl, Y is hydrogen, m is 1, and n is 1.

In certain preferred embodiments, the benzimidazole is located at the 5'-position of the benzotriazole ring.

In certain preferred embodiments, the compound of formula (I) is

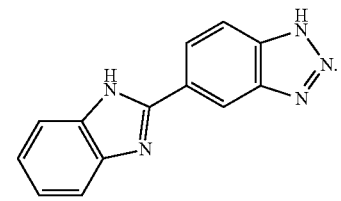 [SMILES: c1ccc2[nH]c(-c3ccc4[nH]nnc4c3)nc2c1]

In certain preferred embodiments, the compound of formula (I) is

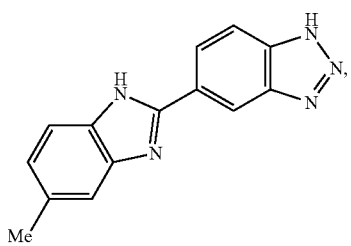

wherein Me is methyl.

In certain preferred embodiments, the compound of formula (I) is

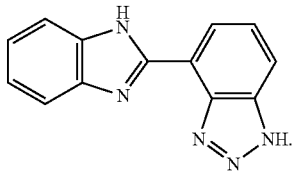 [SMILES: c1ccc2[nH]c(-c3cccc4[nH]nnc34)nc2c1]

In certain preferred embodiments, the compound of formula (I) is

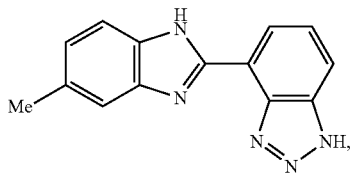

wherein Me is methyl.

In certain embodiments, the compound of formula (I) is a chloride salt, bromide salt, iodide salt, sulfate salt, fluoride salt, perchlorate salt, acetate salt, trifluoroacetate salt, phosphate salt, nitrate salt, carbonate salt, bicarbonate salt, formate salt, chlorate salt, bromated salt, chlorite salt, thiosulfate salt, oxalate salt, cyanide salt, cyanate salt, tetrafluoroborate salt, and the like. In certain preferred embodiments, the compound of formula (I) is a hydrochloride salt or sulfate salt.

In certain preferred embodiments, $R^1$ and/or $R^2$ is hydrogen. While not wishing to be bound by any particular theory, it is postulated that when $R^1$ and/or $R^2$ is hydrogen, hydrogen-bonding can occur between molecules when added to an aqueous system in contact with a metal surface, thereby resulting in enhanced strength of the corrosion inhibitor protective film on the metal surface. Moreover, compounds of formula (I) where $R^1$ and/or $R^2$ is hydrogen generally have increased water solubility.

In certain preferred embodiments, X and Y are individually chosen electron-rich groups and/or alkyl groups. While not wishing to be bound by any particular theory, it is postulated that when X and Y are more electron-rich, the nitrogen atoms in the imidazole and triazole rings may have increased electron density. It is believed that nitrogen atoms having a greater electron density will have stronger coordination with the metal surface of the aqueous system, resulting in a stronger protective film. However, in certain embodiments, X and Y are electron-deficient.

The compounds of formula (I) can be prepared by any suitable synthetic chemical method. One method of preparation is a one-step synthesis using commercially available materials. At elevated temperature, a 1,2-phenylenediamine undergoes condensation with a benzotriazole carboxylic acid in the presence of an acid. For example, benzotriazole-5-carboxylic acid reacts with 4-methyl-o-phenylenediamine in the presence of polyphosphoric acid to form 5-(5-methyl-1H-benzo[d]imidazol-2-yl)-1H-benzo[d][1,2,3]triazole.

Any suitable Lewis or Brönsted acid can be used in the synthesis including, but not limited to, polyphosphoric acid, Eaton's reagent, hydrochloric acid, sulfuric acid, p-toluenesulfonic acid, and triflic acid. In certain preferred embodiments, polyphosphoric acid is used.

A compound of formula (I) can be used to prevent and reduce the corrosion rate of a metal. In an embodiment, the invention provides a method for inhibiting corrosion of a metal surface in contact with an aqueous system, the method comprising adding to the aqueous system a compound of formula (I),

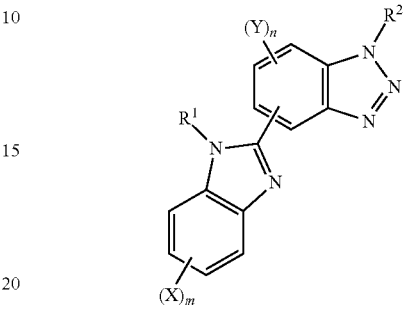

formula (I)

wherein each of X and Y is the same or different, and is selected from the group consisting of hydrogen, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, halosubstituted alkyl, amino, aminoalkyl, cyano, alkoxy, hydroxyl, thiol, alkylthio, carbonyl, nitro, phosphoryl, phosphonyl, and sulfonyl;

each of $R^1$ and $R^2$ is the same or different, and is selected from the group consisting of hydrogen, deuterium, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, hydroxyl, and carbonyl;

m is 1, 2, 3, or 4; and n is 1, 2, or 3;

or a salt thereof.

The compounds of formula (I) may provide corrosion protection for any metal including, but not limited to, copper, iron, silver, steel (e.g., galvanized steel), and aluminum. In certain preferred embodiments, a compound of formula (I) is added to an aqueous system in contact with a metal surface comprising copper to inhibit metal corrosion. In certain preferred embodiments, a compound of formula (I) is added to an aqueous system in contact with a metal surface comprising a copper alloy to inhibit metal corrosion. In certain embodiments, copper complexes with one or more heteroatoms in a compound of formula (I). Copper has a wide-range of applications, including use as copper piping and tubing in plumbing and industrial machinery. Copper and copper alloys are well known for their use in cooling water and boiler water systems.

A compound of formula (I) can be used to protect any copper alloy, including bronze and brass. Bronze commonly comprises copper and tin, but may comprise other elements including aluminum, manganese, silicon, arsenic, and phosphorus. Brass comprises copper and zinc, and is commonly used in piping in water boiler systems. In certain embodiments, a compound of formula (I) is added to an aqueous system in contact with a metal surface comprising bronze to inhibit metal corrosion. In certain embodiments, a compound of formula (I) is added to an aqueous system in contact with a metal surface comprising brass to inhibit metal corrosion. In certain embodiments, a compound of formula (I) is added to an aqueous system in contact with a metal surface comprising a copper-nickel alloy to inhibit metal corrosion.

In certain embodiments, a compound of formula (I) inhibits the corrosion of mild steel. In certain embodiments, a compound of formula (I) inhibits the corrosion of metal alloys including, but not limited to, galvanized steel, stainless steel, cast iron, nickel, and combinations thereof. While not wishing to be bound by any particular theory, it is postulated that the compounds of formula (I) inactivate Cu (II) in solution, preventing the occurrence of galvanic cells on the steel surface. Thus, in certain embodiments, a compound of formula (I) inhibits pitting corrosion of mild steel.

The metal corrosion rate provided by compounds of formula (I) is not limited. In certain embodiments, a compound of formula (I) provides a metal corrosion rate that is acceptable according to industry standards, e.g., about 0.2 mpy or less. In certain preferred embodiments, a compound of formula (I) provides a metal corrosion rate of about 0.1 mpy or less. Thus, in certain preferred embodiments, a compound of formula (I) provides a metal corrosion rate of about 0.1 mpy or less, about 0.05 mpy or less, about 0.04 mpy or less, about 0.03 mpy or less, about 0.02 mpy or less, about 0.01 mpy or less, about 0.005 mpy or less, or about 0.002 mpy or less.

While the compounds of formula (I) can be added to an aqueous system at any dosage rate, the compounds of formula (I) are generally added to an aqueous system at a dosage rate of from about 0.01 ppm to about 500 ppm. In certain embodiments, a compound of formula (I) is added to an aqueous system at a dosage rate of from about 0.01 ppm to about 100 ppm. Thus, in certain preferred embodiments, a compound of formula (I) is added to an aqueous system at a dosage rate of from about 0.01 ppm to about 100 ppm, from about 0.01 ppm to about 75 ppm, from about 0.01 ppm to about 50 ppm, from about 0.01 ppm to about 25 ppm, from about 0.01 ppm to about 10 ppm, from about 0.01 ppm to about 5 ppm, from about 0.1 ppm to about 100 ppm, from about 0.1 ppm to about 75 ppm, from about 0.1 ppm to about 50 ppm, from about 0.1 ppm to about 25 ppm, from about 0.1 ppm to about 10 ppm, from about 0.1 ppm to about 5 ppm, from about 1 ppm to about 100 ppm, from about 1 ppm to about 75 ppm, from about 1 ppm to about 50 ppm, from about 1 ppm to about 25 ppm, from about 1 ppm to about 10 ppm, from about 5 ppm to about 100 ppm, from about 10 ppm to about 100 ppm, from about 25 ppm to about 100 ppm, from about 50 ppm to about 100 ppm, or from about 80 ppm to about 100 ppm.

The compounds of formula (I) can be used to inhibit corrosion of metal in an aqueous system having any pH. In certain preferred embodiments, a compound of formula (I) is added to an aqueous system having a pH of from about 6 to about 12. Thus, in certain preferred embodiments, a compound of formula (I) is added to an aqueous system having a pH of from about 6 to about 12, from about 6 to about 11, from about 6 to about 10, from about 6 to about 9, from about 6 to about 8, from about 7 to about 12, from about 8 to about 12, from about 9 to about 12, from about 7 to about 10, or from about 8 to about 10.

An advantage of the present invention is that compounds of formula (I) generally provide corrosion protection for metal surfaces in the presence of oxidizing halogen compounds. In certain preferred embodiments, a compound of formula (I) provides corrosion protection for metal surfaces in the presence of an oxidizing halogen compound. In certain preferred embodiments, a compound of formula (I) inhibits metal corrosion in the presence of oxidizing halogen compounds including, but not limited to, hypochlorite bleach, chlorine, bromine, hypochlorite, hypobromite, chlorine dioxide, iodine/hypoiodous acid, hypobromous acid, halogenated hydantoins, stabilized versions of hypochlorous or hypobromous acids, or combinations thereof.

As discussed above, the compounds of formula (I) provide protection against corrosion in the presence of oxidizing halogen compounds. While not wishing to be bound by any particular theory, it is postulated that the additional number of nitrogen atoms of the corrosion inhibitors of formula (I) provide a greater number of sites for bonding to metal surfaces and metal ions, which can provide enhanced protection as compared to many existing corrosion inhibitors.

In certain embodiments, the compounds of formula (I) surprisingly and unexpectedly provide lower corrosion rates for copper in the presence of oxidizing halogen compounds when compared to many commonly used corrosion inhibitors. For example, in the presence of bleach, inventive corrosion inhibitor 5-(1H-benzo[d]imidazol-2-yl)-1H-benzo[d][1,2,3]triazole (BMDZ-BZT) provides greater copper corrosion resistance than either benzimidazole (BMDZ) or benzotriazole (BZT). In other words, covalently bonded benzimidazole-benzotriazole provides greater resistance to corrosion in the presence of a oxidizing halogen compound than benzimidazole and benzotriazole individually.

In certain preferred embodiments, a compound of formula (I) inhibits corrosion of copper in the presence of oxidizing halogen compounds including, but not limited to, hypochlorite bleach, chlorine, bromine, hypochlorite, hypobromite, chlorine dioxide, iodine/hypoiodous acid, hypobromous acid, halogenated hydantoins, stabilized versions of hypochlorous or hypobromous acids, or combinations thereof.

The metal corrosion rate provided by compounds of formula (I) in the presence of an oxidizing compound is not limited. In certain embodiments, a compound of formula (I) provides a metal corrosion rate in the presence of an oxidizing halogen compound of about 0.2 mpy or less. In certain preferred embodiments, a compound of formula (I) provides a metal corrosion rate in the presence of an oxidizing halogen compound of about 0.1 mpy or less. Thus, in certain preferred embodiments, a compound of formula (I) provides a metal corrosion rate in the presence of an oxidizing halogen compound of about 0.1 mpy or less, about 0.05 mpy or less, about 0.04 mpy or less, about 0.03 mpy or less, about 0.02 mpy or less, about 0.01 mpy or less, about 0.005 mpy or less, or about 0.002 mpy or less. In certain preferred embodiments, the metal corrosion rate provided by a compound of formula (I) is essentially the same in the absence or presence of an oxidizing halogen compound.

In certain embodiments, a compound of formula (I) inhibits metal corrosion when added to an aqueous system comprising a non-halogen-containing oxidizing biocide including, but not limited to, peroxides (e.g., hydrogen peroxide), persulfates, permanganates, and peracetic acids.

Another advantage of using the compounds of formula (I) is a smaller amount of oxidizing halogen compound is required to maintain low microbial levels because the compounds of formula (I) generally has reduced interaction with the oxidizing halogen compound. Furthermore, halogenated azoles that result from the reaction between an azole and oxidizing agent are known to be environmentally undesirable due to their toxicity. Thus, another advantage of the present invention is that the compounds of formula (I) are resistant or essentially resistant to halogen attack, and do not lead to the release of halogenated azoles into the environment.

In certain preferred embodiments, the aqueous system is a cooling water system. The cooling water system can be a closed loop cooling water system or an open loop cooling water system. In certain preferred embodiments, a compound of formula (I) is added to a closed loop cooling water system at a dosage rate of from about 0.01 ppm to about 200 ppm. In certain preferred embodiments, a compound of formula (I) is added to an open loop cooling water system at a dosage rate of from about 0.01 ppm to about 20 ppm.

The compounds of formula (I) are contacted with a metal surface by any suitable method. In certain embodiments, a solution of a compound of formula (I) is contacted with a metal surface by immersion, spraying, or other coating techniques. In certain preferred embodiments, a solution of a compound of formula (I) is introduced into the water of the aqueous system by any conventional method and is fed into the aqueous system on either a periodic or continuous basis.

In certain embodiments, if a compound of formula (I) is relatively insoluble in water, the compound may be made soluble by forming an organic or inorganic salt of the compound. Thus, in certain embodiments, a compound of formula (I) is a water-soluble salt. In certain embodiments, a compound of formula (I) is added as a solution in a water-miscible co-solvent including, but not limited to, acetone, methanol, ethanol, propanol, formic acid, formamide, propylene glycol, or ethylene glycol. In certain embodiments, a co-solvent is used to achieve maximum solubility of a compound of formula (I) in the aqueous system. In certain embodiments, low molecular weight polyethylene glycol, polypropylene glycol, a surfactant (e.g., organic sulfonic acid), or combinations thereof are used to increase the solubility of a compound of formula (I).

Those skilled in the art will appreciate that the compounds of formula (I) can be added to an aqueous system alone or in combination with other corrosion inhibitors or treatment chemicals. Multiple corrosion inhibitors can be dosed as a combined corrosion inhibitor formulation or each corrosion inhibitor can be added separately, including two or more compounds of formula (I). Moreover, the compounds of formula (I) can be added to an aqueous system in combination with a variety of additional corrosion inhibitors including, but not limited to, triazoles, benzotriazoles (e.g., benzotriazole or tolyltriazole), benzimidazoles, orthophosphate, polyphosphates, phosphonates, molybdates, silicates, oximes, and nitrites. The compounds of formula (I) also can be added to an aqueous system in combination with a variety of additional additives, such as treatment polymers, antimicrobial agents, anti-scaling agents, colorants, fillers, buffers, surfactants, viscosity modifiers, chelating agents, dispersants, deodorants, masking agents, oxygen scavengers, and indicator dyes.

The compounds of formula (I) can be added to an aqueous system in any form. In certain embodiments, a compound of formula (I) is added to an aqueous system as a dried solid. In certain embodiments, a compound of formula (I) is added to an aqueous system as a solution in a co-solvent miscible with water. In certain preferred embodiments, a compound of formula (I) is added to an aqueous system as an aqueous solution.

In certain embodiments, a compound of formula (I) is added to a laundry system or a warewashing system.

In certain embodiments, a compound of formula (I) is added to an aqueous system that recirculates water. In certain embodiments, a compound of formula (I) is added to an aqueous system that has stagnant water.

The following examples further illustrate the invention but, of course, should not be construed as in any way limiting its scope.

Example 1

This Example illustrates a method of synthesis of compounds of formula (I) in accordance with an embodiment of the invention.

General Chemistry Methods. The reactions were performed under positive pressure of nitrogen with oven-dried glassware. Polyphosphoric acid, benzotriazole-5-carboxylic acid, and 4-methyl-o-phenylenediamine were purchased from Sigma-Aldrich (St. Louis, Mo.). NMR analysis was performed on a Brücker 400 Hz spectrometer at room temperature.

Synthesis of 5-(5-methyl-1H-benzo[d]imidazol-2-yl)-1H-benzo[d][1,2,3]triazole

A roundbottom flask was charged with 4-methyl-o-phenylenediamine (0.100 mmol, 12.2 g), benzotriazole-5-carboxylic acid (0.100 mol, 16.3 g), and polyphosphoric acid (40 g). The reaction mixture was heated at 160° C. for 6 hours. After completion, the reaction mixture was poured into cold water and quenched with NaOH (10% aq. solution) until precipitation occurred. The precipitate was filtered and washed with cold water, yielding the title compound as a pure sea green colored solid (18.8 g, 80%).

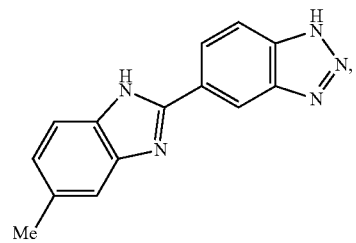

wherein Me is methyl.

$^1$H NMR (400 MHz, DMSO-D6) δ 2.49 (s, 3H), 7.1 (d, 1H), 7.4 (s, 1H), 7.5 (d, 1H), 8.0 (d, 1H), 8.3 (d, 1H), 8.7 (s, 1H); $^{13}$C NMR (100 MHz, DMSO-D6) δ 21.2, 112.7, 115.3, 123.6, 124.3, 127.5, 131.4, 139.3, 150.6.

Example 2

This Example illustrates the corrosion rate of copper in the presence of known corrosion inhibitors and compounds of formula (I) in accordance with certain embodiments of the invention.

The corrosion rate of copper in the presence of inventive corrosion inhibitors 5-(1H-benzo[d]imidazol-2-yl)-1H-benzo[d][1,2,3]triazole (i.e., 5-benzimidazole benzotriazole) and 5-(5-methyl-1H-benzo[d]imidazol-2-yl)-1H-benzo[d][1,2,3]triazole (i.e., 5-(5-methylbenzimidazole benzotriazole) was determined using linear polarization resistance measurements. In addition, the corrosion rate of copper in the presence of known corrosion inhibitors benzimidazole, benzotriazole, tolyltriazole, and 2-phenylbenzimidazole was determined using linear polarization resistance measurements. The inventive compounds were prepared according to the method of Example 1. Benzimidazole, 2-phenylbenzimidazole, benzotriazole, and tolyltriazole were purchased from Sigma-Aldrich (St. Louis, Mo.).

For each experiment, cylindrical copper coupons prepolished using SIC 600 paper and fitted on a Pine rotator were immersed in a solution of corrosion inhibitor. The test solution comprised 470 ppm calcium, 230 ppm magnesium, 590 ppm chloride, 260 ppm sulfate, and 100 ppm alkalinity, as $CaCO_3$. The pH of the test water was maintained at 7.0 using carbon dioxide, and the water temperature was maintained at 45° C. throughout the experiment.

The copper samples were immersed in 1 liter electrochemical cells comprising a 5 ppm inhibitor solution, and the Rp (polarization resistance) was recorded over a 24 hour period. The analysis was conducted using the following testing conditions: Initial E: −0.02V; Final E: +0.02V; Scan rate: 0.5 mV/s; Sample period: 1 second; Repeat time: 15 minutes; Sample area: 5 $cm^2$; Density: 8.92 $g/cm^3$.

After 24 hours, the copper samples were exposed to a 25% bleach solution. After the FRC reached 1 ppm, the copper samples were analyzed over a 24 hour period. Throughout the analysis, the bleach solution was maintained at 1 ppm FRC. The Rp in the absence and presence of bleach was collected and analyzed, and the average corrosion rate was calculated and recorded in Table 1. Corrosion rates were calculated in mils per year (mpy). FIGS. 1-4 displays data plots for compounds 1-4.

Figure 2:
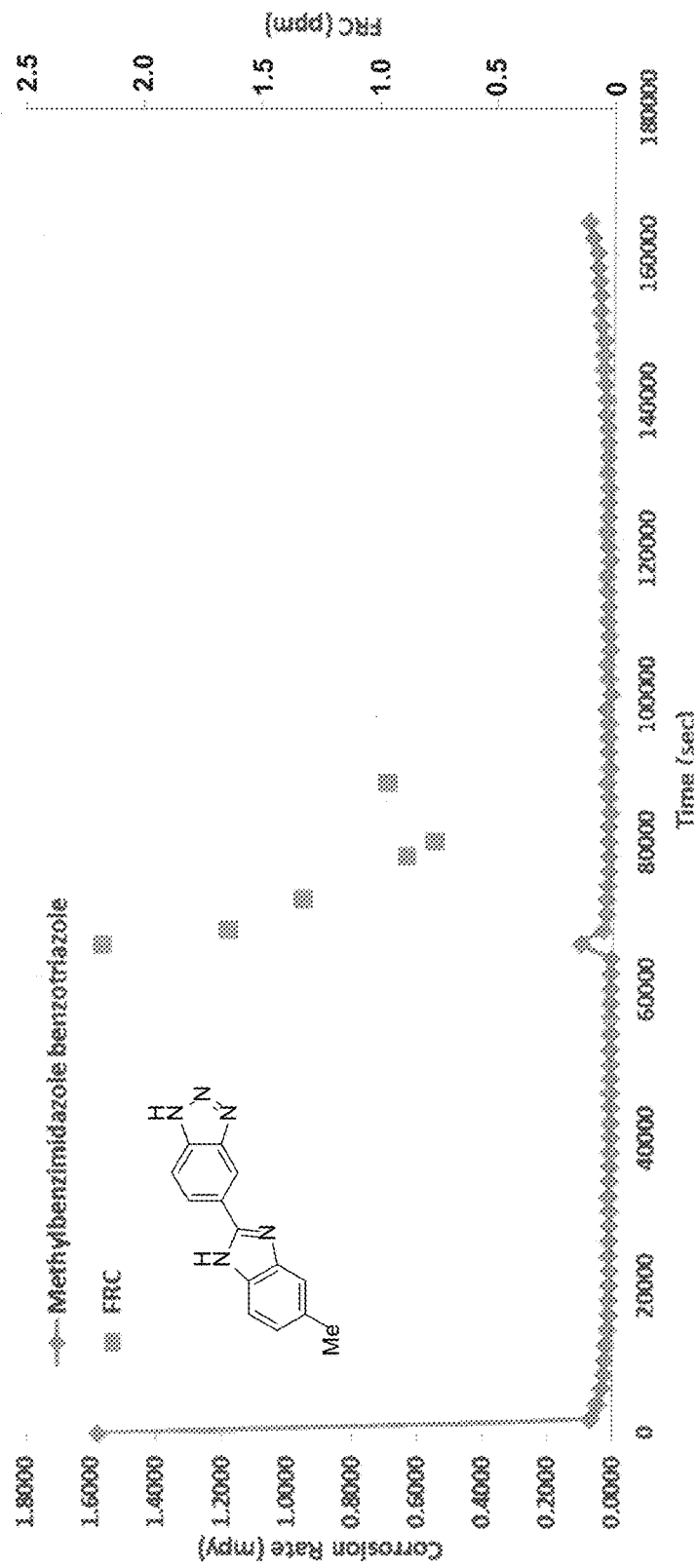
FIG. 2 is a line graph that illustrates the corrosion rate of copper using 5-(5-methyl-1H-benzo[d]imidazol-2-yl)-1H-benzo[d][1,2,3]triazole (5-(5-methylbenzimidazole) benzotriazole) as a corrosion inhibitor in the absence and presence of bleach.
Figure 3:
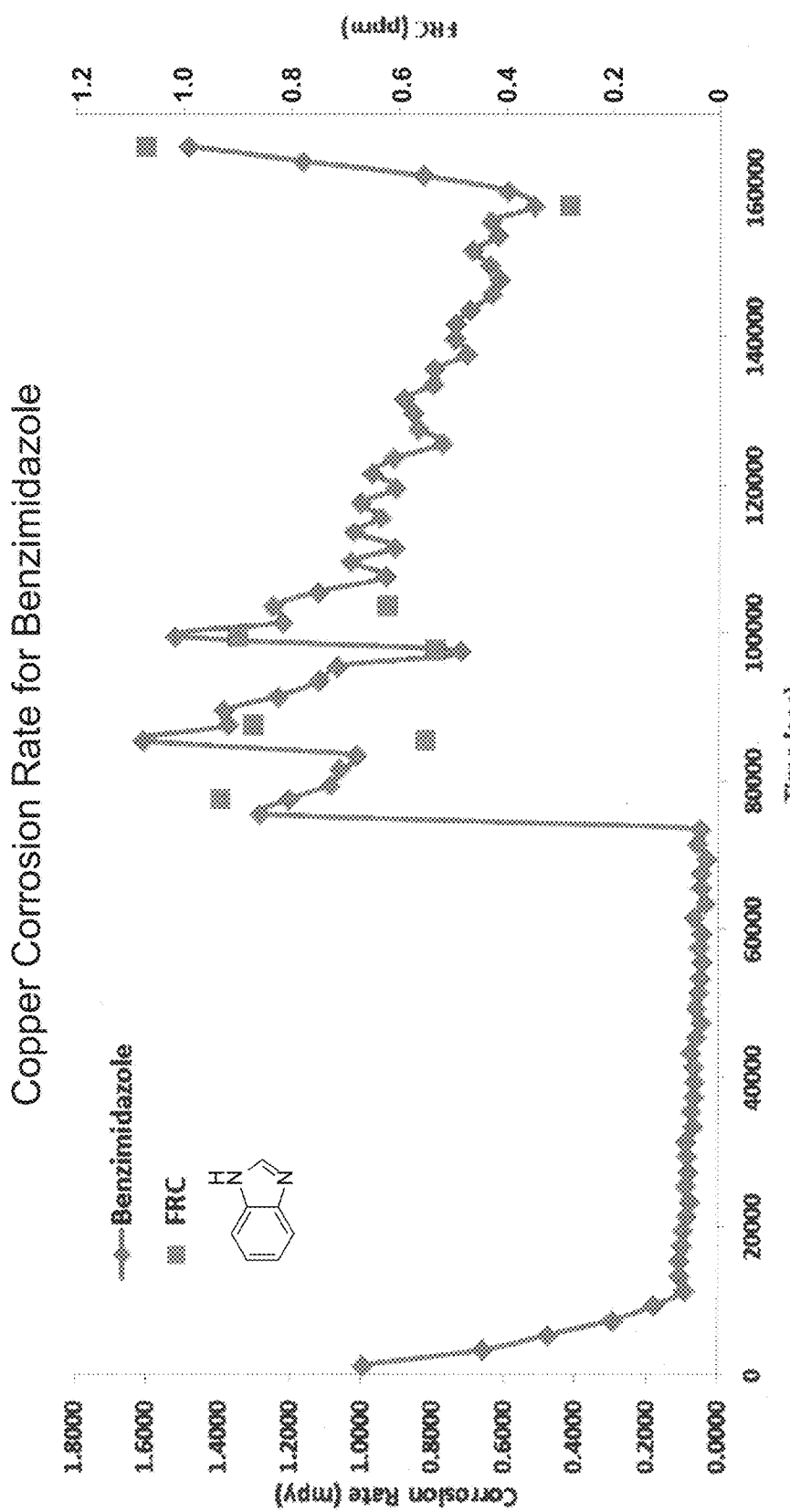
FIG. 3 is a line graph that illustrates the corrosion rate of copper using benzimidazole as a corrosion inhibitor in the absence and presence of bleach.
Figure 4:
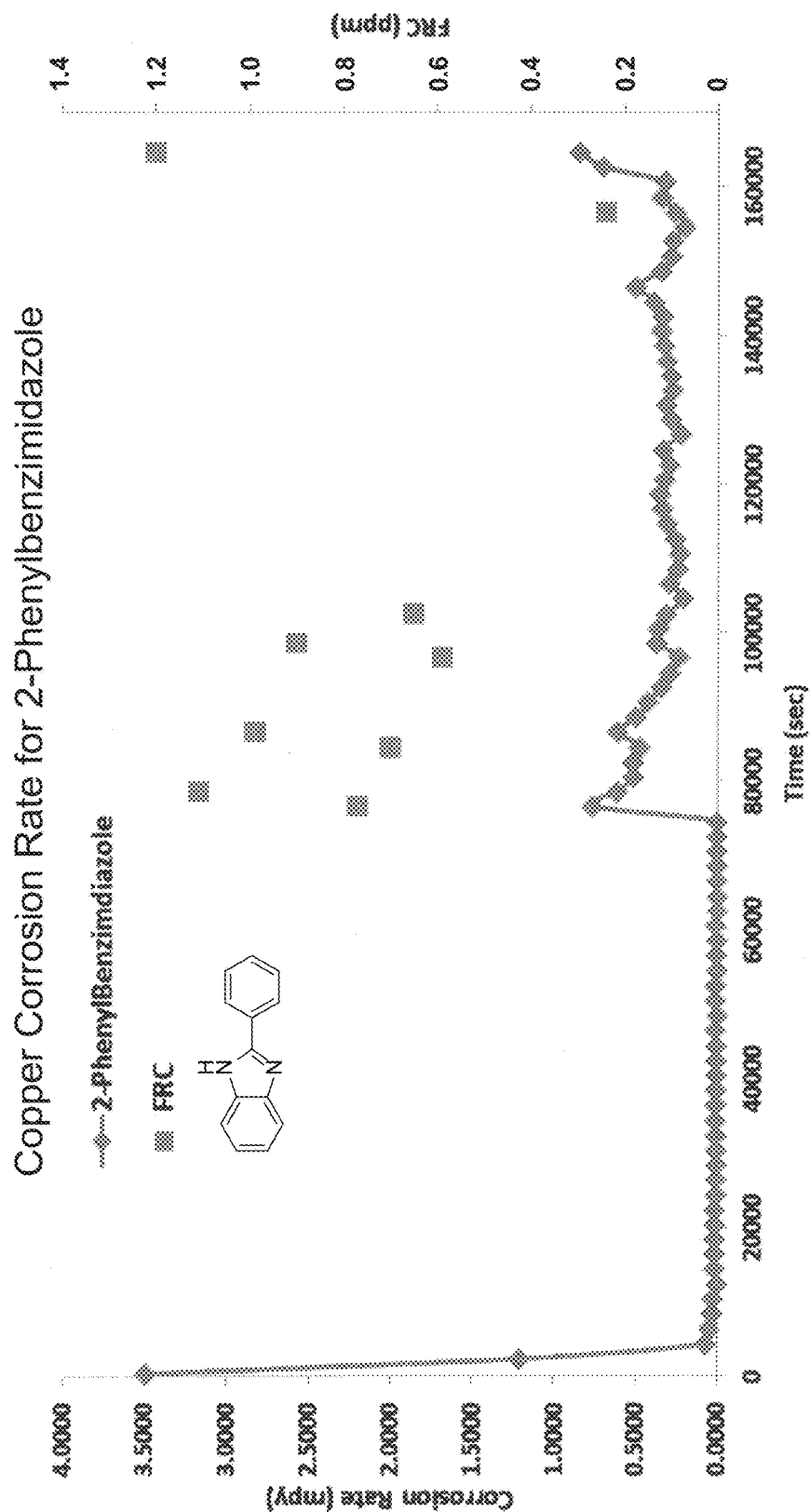
FIG. 4 is a line graph that illustrates the corrosion rate of copper using 2-phenylbenzimidazole as a corrosion inhibitor in the absence and presence of bleach.

As shown in Table 1 and FIGS. 1 and 2, the inventive corrosion inhibitors (i.e., compounds 1 and 2) greatly decrease the corrosion rate of copper. Moreover, the corrosion rate of copper in the presence of inventive compounds 1 and 2 is comparable to commonly used tolyltriazole (TT). Upon the addition of bleach, the corrosion rate provided by the inventive corrosion inhibitors remained relatively constant. For example, the corrosion rate observed for BMDZ-BZT was 0.0177 mpy in the absence of bleach and 0.0171 mpy in the presence of bleach.

In contrast, the corrosion rates of the known corrosion inhibitors (i.e., compounds 3-7) generally increase in the presence of bleach. It was surprisingly and unexpectedly found that BMDZ-BZT (i.e., compound 1) yields an average corrosion rate in the presence of bleach lower than both BMDZ and BZT individually. Copper in the presence of benzimidazole (BMDZ) and benzotriazole (BZT) with bleach had an average corrosion rate of 0.9594 mpy and 0.0594 mpy, respectively.

This Example illustrates that a compound of formula (I) can reduce the rate of copper corrosion. Furthermore, compounds of the present invention provide excellent corrosion resistance in the presence of an oxidizing halogen. The corrosion inhibitory properties of the corrosion inhibitors of a compound of formula (I) do not erode in the presence of an oxidizing halogen compound. Moreover, this Example illustrates that benzimidazole-benzotriazole corrosion inhibitors provide greater corrosion resistance than benzimidazole and benzotriazole individually.

TABLE 1

| Compound No. | Compound Name | No FRC Corrosion Rate (mpy) | 1 ppm FRC Corrosion Rate (mpy) |
|---|---|---|---|
| 1 | 5-(1H-benzo[d]imidazol-2-yl)-1H-benzo[d][1,2,3]triazole (BMDZ-BZT) | 0.0177 | 0.0171 |
| 2 | 5-(5-methyl-1H-benzo[d]imidazol-2-yl)-1H-benzo[d][1,2,3]triazole | 0.0090 | 0.0214 |
| 3 | Benzimidazole (BMDZ) | 0.0890 | 0.9594 |
| 4 | 2-phenylbenzimidazole | 0.0128 | 0.3726 |
| 5 | 5-carboxybenzotriazole | 0.1487 | 0.5631 |
| 6 | Benzotriazole (BZT) | 0.0032 | 0.0594 |
| 7 | Tolyltriazole (TT) | 0.0214 | 0.0995 |

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:
1. A compound of formula (I):

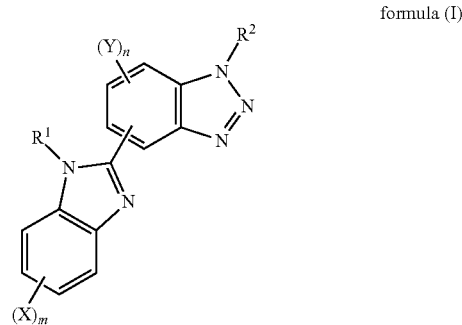

formula (I)

wherein each of X and Y is the same or different, and is selected from the group consisting of hydrogen, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, halosubstituted alkyl, amino, aminoalkyl, cyano, alkoxy, hydroxyl, thiol, alkylthio, carbonyl, nitro, phosphoryl, phosphonyl, and sulfonyl;

each of $R^1$ and $R^2$ is the same or different, and is selected from the group consisting of hydrogen, deuterium, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, hydroxyl, and carbonyl;

m is 1, 2, 3, or 4; and n is 1, 2, or 3;

or a salt thereof.

2. The compound of claim 1, wherein $R^1$ and $R^2$ are hydrogen.

3. The compound of claim 1, wherein X and Y are hydrogen.

4. The compound of claim 1, wherein X is $C_1$-$C_{16}$ alkyl, Y is hydrogen, m is 1, and n is 1.

5. The compound of claim 1, wherein the compound of formula (I) is

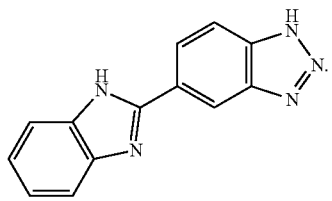 [SMILES: c1ccc2[nH]c(-c3ccc4[nH]nnc4c3)nc2c1]

6. The compound of claim 1, wherein the compound of formula (I) is

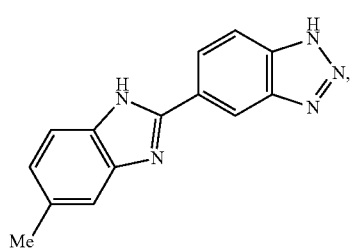

wherein Me is methyl.

7. The compound of claim 1, wherein the compound of formula (I) is

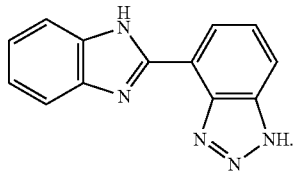 [SMILES: c1ccc2[nH]c(-c3cccc4[nH]nnc34)nc2c1]

8. The compound of claim 1, wherein the compound of formula (I) is

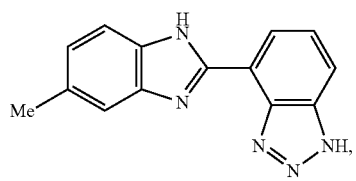

wherein Me is methyl.

9. A method for inhibiting corrosion of a metal surface in contact with an aqueous system, the method comprising adding to the aqueous system a compound of formula (I),

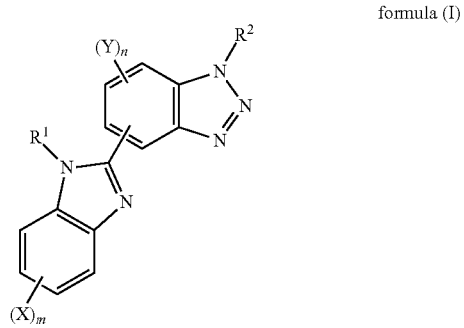

formula (I)

wherein each of X and Y is the same or different, and is selected from the group consisting of hydrogen, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, halosubstituted alkyl, amino, aminoalkyl, cyano, alkoxy, hydroxyl, thiol, alkylthio, carbonyl, nitro, phosphoryl, phosphonyl, and sulfonyl;

each of $R^1$ and $R^2$ is the same or different, and is selected from the group consisting of hydrogen, deuterium, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, hydroxyl, and carbonyl;

m is 1, 2, 3, or 4; and n is 1, 2, or 3;

or a salt thereof.

10. The method of claim 9, wherein the compound of formula (I) is

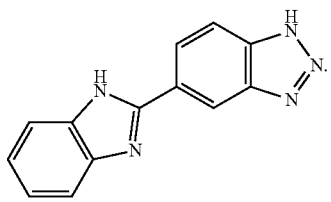 [SMILES: c1ccc2[nH]c(-c3ccc4[nH]nnc4c3)nc2c1]

11. The method of claim 9, wherein the compound of formula (I) is

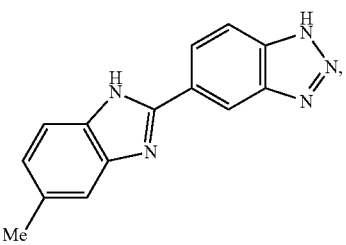

wherein Me is methyl.

12. The method of claim 9, wherein the compound of formula (I) is

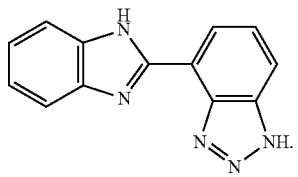 [SMILES: c1ccc2[nH]c(-c3cccc4[nH]nnc34)nc2c1]

13. The method of claim 9, wherein the metal surface comprises copper or a copper alloy.
14. The method of claim 9, wherein the aqueous system comprises an oxidizing halogen compound.
15. The method of claim 9, wherein the compound of formula (I) is added to the aqueous system at a dosage of from about 0.01 ppm to about 100 ppm.
16. The method of claim 9, wherein the aqueous system has a pH of from about 6 to about 12.
17. The method of claim 9, wherein the aqueous system is a cooling water system.
18. The method of claim 17, wherein the cooling water system is a closed loop cooling water system.
19. The method of claim 17, wherein the cooling water system is an open loop cooling water system.
20. The method of claim 9, wherein the metal has a corrosion rate of about 0.1 mpy or less.

* * * * *